US008233990B2

(12) United States Patent
Goetz (10) Patent No.: US 8,233,990 B2
(45) Date of Patent: Jul. 31, 2012

(54) SELECTION OF NEUROSTIMULATOR PARAMETER CONFIGURATIONS USING DECISION TREES (75) Inventor: Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 576 days.

(21) Appl. No.: 12/559,090

(22) Filed: Sep. 14, 2009

(65) Prior Publication Data
US 2010/0070001 A1 Mar. 18, 2010

Related U.S. Application Data (62) Division of application No. 10/767,545, filed on Jan. 29, 2004, now Pat. No. 7,617,002.

(60) Provisional application No. 60/503,209, filed on Sep. 15, 2003.

(51) Int. Cl.
*A61N 1/00* (2006.01)

(52) U.S. Cl. ............... 607/59; 607/39; 607/40; 607/45; 607/46; 607/117

(58) Field of Classification Search .............. 607/2, 39, 607/40, 45, 46, 47, 115–117, 59
See application file for complete search history.

(56) References Cited

U.S. PATENT DOCUMENTS

| 4,872,122 | A | 10/1989 | Altschuler et al. |
| 4,895,574 | A | 1/1990 | Rosenberg |
| 5,005,143 | A | 4/1991 | Altschuler et al. |
| 5,240,009 | A | 8/1993 | Williams |
| 5,280,792 | A | 1/1994 | Leong et al. |
| 5,358,513 | A | 10/1994 | Powell, III et al. |
| 5,383,910 | A | 1/1995 | den Dulk |
| 5,443,486 | A | 8/1995 | Hrdlicka et al. |
| 5,522,863 | A | 6/1996 | Spano et al. |
| 5,626,140 | A | 5/1997 | Feldman et al. |
| 5,645,069 | A | 7/1997 | Lee |
| 5,673,367 | A | 9/1997 | Buckley |
| 5,702,429 | A | 12/1997 | King |
| 5,706,403 | A | 1/1998 | Shibata et al. |

(Continued)

FOREIGN PATENT DOCUMENTS

EP 0 653 224 5/1995

(Continued)

OTHER PUBLICATIONS

Notification of Transmittal of the International Preliminary Examination Report dated Nov. 2, 2005, International Application No. PCT/US2004/030138, (9 pages).

(Continued)

*Primary Examiner* — Mark W Bockelman
(74) *Attorney, Agent, or Firm* — Shumaker & Sieffert, PA (57) ABSTRACT

A selection of parameter configurations for a neurostimulator using decision trees may be employed by a programming device to allow a clinician or other user to select parameter configurations, and then program an implantable neurostimulator to deliver therapy using the selected parameter configurations. The programming device executes a parameter configuration search algorithm to guide the clinician in selection of parameter configurations. The search algorithm relies on a decision tree to identify optimum parameter configurations. A decision tree is useful in classifying observations in a data set based upon one or more attributes or fields within the data. The data set includes parameter configurations matched with observed ratings of efficacy on patients of a similar indication. The learned attribute, on which classification occurs, will be the optimum parameter configuration for a set of rated configurations used to produce the classification. The decision trees may be especially useful in identifying electrode configurations.

18 Claims, 6 Drawing Sheets

U.S. PATENT DOCUMENTS

| | | | |
|---|---|---|---|
| 5,713,932 A | 2/1998 | Gillberg et al. | |
| 5,716,382 A | 2/1998 | Snell | |
| 5,774,357 A | 6/1998 | Hoffberg et al. | |
| 5,782,885 A | 7/1998 | Andersson | |
| 5,810,014 A | 9/1998 | Davis et al. | |
| 5,867,386 A | 2/1999 | Hoffberg et al. | |
| 5,875,108 A | 2/1999 | Hoffberg et al. | |
| 5,901,246 A | 5/1999 | Hoffberg et al. | |
| 5,903,454 A | 5/1999 | Hoffberg et al. | |
| 5,920,477 A | 7/1999 | Hoffberg et al. | |
| 5,921,937 A | 7/1999 | Davis et al. | |
| 5,938,688 A | 8/1999 | Schiff | |
| 5,995,868 A | 11/1999 | Dorfmeister et al. | |
| 5,999,854 A | 12/1999 | Deno et al. | |
| 6,081,750 A | 6/2000 | Hoffberg et al. | |
| 6,129,745 A | 10/2000 | Sun et al. | |
| 6,171,239 B1 | 1/2001 | Humphrey | |
| 6,192,273 B1 | 2/2001 | Igel et al. | |
| 6,263,230 B1 | 7/2001 | Haynor et al. | |
| 6,269,267 B1 | 7/2001 | Bardy et al. | |
| 6,304,773 B1 | 10/2001 | Taylor et al. | |
| 6,345,200 B1 | 2/2002 | Mouchawar et al. | |
| 6,370,423 B1 | 4/2002 | Guerrero et al. | |
| 6,370,428 B1 | 4/2002 | Snyder et al. | |
| 6,385,479 B1 | 5/2002 | Sibbitt et al. | |
| 6,386,882 B1 | 5/2002 | Linberg | |
| 6,400,996 B1 | 6/2002 | Hoffberg et al. | |
| 6,408,290 B1 | 6/2002 | Thiesson et al. | |
| 6,418,424 B1 | 7/2002 | Hoffberg et al. | |
| 6,434,261 B1 | 8/2002 | Zhang et al. | |
| 6,456,622 B1 | 9/2002 | Skaanning et al. | |
| 6,473,653 B1 | 10/2002 | Schallhorn et al. | |
| 6,480,743 B1 | 11/2002 | Kirkpatrick et al. | |
| 6,480,814 B1 | 11/2002 | Levitan | |
| 6,496,816 B1 | 12/2002 | Thiesson et al. | |
| 6,497,655 B1 | 12/2002 | Linberg et al. | |
| 6,522,928 B2 | 2/2003 | Whitehurst et al. | |
| 6,530,954 B1 | 3/2003 | Eckmiller | |
| 6,539,263 B1 | 3/2003 | Schiff et al. | |
| 6,547,746 B1 | 4/2003 | Marino | |
| 6,549,804 B1 | 4/2003 | Osorio et al. | |
| 6,554,762 B2 | 4/2003 | Leysieffer | |
| 6,556,699 B2 | 4/2003 | Rogers et al. | |
| 6,572,542 B1 | 6/2003 | Houben et al. | |
| 6,575,894 B2 | 6/2003 | Leysieffer et al. | |
| 6,597,943 B2 | 7/2003 | Taha et al. | |
| 6,609,017 B1 | 8/2003 | Shenoy et al. | |
| 6,658,287 B1 | 12/2003 | Litt et al. | |
| 6,659,968 B1 | 12/2003 | McClure | |
| 6,662,051 B1 | 12/2003 | Eraker et al. | |
| 6,697,672 B2 | 2/2004 | Andersson | |
| 6,704,595 B2 | 3/2004 | Bardy | |
| 7,123,961 B1 | 10/2006 | Kroll et al. | |
| 2002/0016699 A1 | 2/2002 | Hoggart et al. | |
| 2002/0038294 A1 | 3/2002 | Matsugu | |
| 2002/0045804 A1 | 4/2002 | Christopher et al. | |
| 2002/0055779 A1 | 5/2002 | Andrews | |
| 2002/0087201 A1 | 7/2002 | Firlik et al. | |
| 2002/0091419 A1 | 7/2002 | Firlik et al. | |
| 2002/0103512 A1 | 8/2002 | Echauz et al. | |
| 2002/0123673 A1 | 9/2002 | Webb et al. | |
| 2002/0138013 A1 | 9/2002 | Guerrero et al. | |
| 2002/0151992 A1 | 10/2002 | Hoffberg et al. | |
| 2003/0041866 A1 | 3/2003 | Linberg et al. | |
| 2003/0043815 A1 | 3/2003 | Tinsley et al. | |
| 2003/0050568 A1 | 3/2003 | Green et al. | |
| 2003/0053663 A1 | 3/2003 | Chen et al. | |
| 2003/0088274 A1 | 5/2003 | Gliner et al. | |
| 2003/0093129 A1 | 5/2003 | Nicolelis et al. | |
| 2003/0097159 A1 | 5/2003 | Schiff et al. | |
| 2003/0097161 A1 | 5/2003 | Firlik et al. | |
| 2003/0105409 A1 | 6/2003 | Donoghue et al. | |
| 2003/0158587 A1 | 8/2003 | Esteller et al. | |
| 2003/0195569 A1 | 10/2003 | Swerdlow et al. | |
| 2003/0216654 A1 | 11/2003 | Xu et al. | |
| 2004/0103001 A1 | 5/2004 | Mazar et al. | |
| 2004/0129271 A1 | 7/2004 | Hickle | |

FOREIGN PATENT DOCUMENTS

| | | |
|---|---|---|
| EP | 0 796 636 | 9/1997 |
| EP | 0 684 858 | 4/1998 |
| EP | 0 848 965 | 6/1998 |
| EP | 0 882 469 | 12/1998 |
| EP | 1 192 971 | 4/2002 |
| WO | WO 00/10455 | 3/2000 |
| WO | WO 01/17419 | 3/2001 |
| WO | WO 01/43823 | 6/2001 |
| WO | WO 01/56467 | 8/2001 |
| WO | WO 01/60445 | 8/2001 |
| WO | WO 01/82995 | 11/2001 |
| WO | WO 02/02622 | 1/2002 |
| WO | WO 02/15777 | 2/2002 |
| WO | WO 03/033070 | 4/2003 |
| WO | WO 03/037231 | 5/2003 |
| WO | WO 03/094721 | 11/2003 |
| WO | WO 2004/031919 | 4/2004 |

OTHER PUBLICATIONS

Office Action dated Mar. 29, 2010 for U.S. Appl. No. 11/824,219 (10 pgs.).

Responsive Amendment dated Jun. 29, 2010 for U.S. Appl. No. 11/824,219 (15 pgs.).

SELECTION OF NEUROSTIMULATOR PARAMETER CONFIGURATIONS USING DECISION TREES

This application is a divisional of U.S. application Ser. No. 10/767,545, filed on Jan. 29, 2004, which claims the benefit of U.S. Provisional Application Ser. No. 60/503,209, filed Sep. 15, 2003. The entire content of both of these applications is incorporated herein by reference.

TECHNICAL FIELD

The invention relates to neurostimulation therapy and, more particularly, to techniques for selection of parameter configurations for an implantable neurostimulator.

BACKGROUND

Implantable medical devices are used to deliver neurostimulation therapy to patients to treat a variety of symptoms or conditions such as chronic pain, tremor, Parkinson's disease, epilepsy, incontinence, sexual dysfunction, or gastroparesis. The implantable medical device delivers neurostimulation therapy via one or more leads that include electrodes located proximate to the spinal cord, pelvic nerves, sacrum, or stomach, or within the brain of a patient. In general, the implantable medical device delivers neurostimulation therapy in the form of electrical pulses.

A clinician selects values for a number of programmable parameters in order to define a parameter configuration for the neurostimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient, and duration for which the stimulation energy is delivered. In addition, the clinician also selects particular electrodes within an electrode set to be used to deliver the pulses, and the polarities of the selected electrodes. The electrode combinations and polarities may be referred to as an electrode configuration. Hence, a parameter configuration may involve one or more of a variety of parameters including electrode configuration, amplitude, pulse width, pulse rate, and duration.

The process of selecting parameter configurations can be time consuming, and may require a great deal of trial and error before an optimum electrode configuration is discovered. The optimum parameter configuration may be better than other configurations in balancing clinical results and side effects experienced by the patient. This balance represents overall efficacy of a parameter configuration. The process for selecting parameter configurations can be difficult due to the combinatorial possibilities of parameters, the complexity of the underlying biophysics, and subjective and possibly inconsistent feedback from the patient concerning observed efficacy for a given parameter configuration.

SUMMARY

In general, the invention is directed to a technique for selection of parameter configurations for a neurostimulator using decision trees. The technique may be employed by a programming device to allow a clinician to select parameter configurations, and then program an implantable neurostimulator to deliver therapy using the selected parameter configurations.

A parameter configuration may define one or more parameters for delivery of neurostimulation, such as electrode configuration, amplitude, pulse width, pulse rate, or duration. For example, the parameter configurations may define electrode configurations that specify electrode combinations and polarities for an electrode set implanted in a patient. The electrode set may be carried by one or more implanted leads that are electrically coupled to the neurostimulator. In some embodiments, the parameter configurations may further define one or more parameters such as amplitudes, pulse widths, pulse rates, and durations of stimulation energy delivered by electrodes in the electrode configuration.

In operation, the programming device executes a parameter configuration search algorithm to guide the clinician in the selection of parameter configurations. The search algorithm relies on a decision tree to identify potential optimum parameter configurations, such as electrode configurations within an electrode set. The decision tree provides guidance in the electrode configuration selection process, interactively guiding the clinician by suggesting the configurations that are most likely to be efficacious given the results of determinations along the path of the decision tree based on efficacy observations already performed during an evaluation session.

A decision tree is useful in classifying observations in a data set based upon one or more attributes or fields within the data. Decision trees can be built by hand by experts in the field or can be learned from the data sets themselves using existing algorithms, e.g., ID3, C4.5, and the like.

In accordance with the invention, hierarchical decision trees, which are either learned or designed, guide the process of parameter optimization. The data set includes parameter configurations matched with observed ratings of efficacy on patients of a similar symptomatic indication. The learned attribute, on which classification occurs, will be the optimum parameter configuration for a given set of rated configurations, which are used to produce the classification. The decision trees may be especially useful in identifying electrode configurations. With the aid of the decision trees, a programming device provides a clinician with suggestions of which configurations are most likely to be efficacious.

In one embodiment, the invention provides a method comprising selecting a first parameter configuration for a neurostimulator, receiving an indication of observed efficacy of the first parameter configuration, and selecting a second parameter configuration for the neurostimulator based on the indication of observed efficacy and a set of additional electrode configurations identified by a decision tree.

In another embodiment, the invention provides a computer-readable medium comprising instructions to cause a processor to select a first parameter configuration for a neurostimulator, receive an indication of observed efficacy of the first parameter configuration, and select a second parameter configuration for the neurostimulator based on the indication of observed efficacy and a set of additional electrode configurations identified by a decision tree.

In a further embodiment, the invention provides a device comprising a processor programmed to select a first parameter configuration for a neurostimulator, receive an indication of observed efficacy of the first parameter configuration, and select a second parameter configuration for the neurostimulator based on the indication of observed efficacy and a set of additional electrode configurations identified by a decision tree.

The invention may provide a number of advantages. For example, the invention may allow a clinician to more quickly identify desirable parameter configurations such as electrode combinations, reducing the overall amount of time the clinician spends programming neurostimulation therapy for a patient. In contrast to random or idiosyncratic search techniques, a technique based on decision trees is capable of learning from the evaluation of earlier parameter configurations, and developing a decision tree that is more likely to lead to an optimum configuration. In general, the invention can reduce the length of a programming session for the clinician and the patient, and support selection of optimum electrode configurations to achieve overall efficacy. In addition, with the invention, it may be possible to identify optimal or near optimal parameter configurations that otherwise might not be identified by the clinician.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
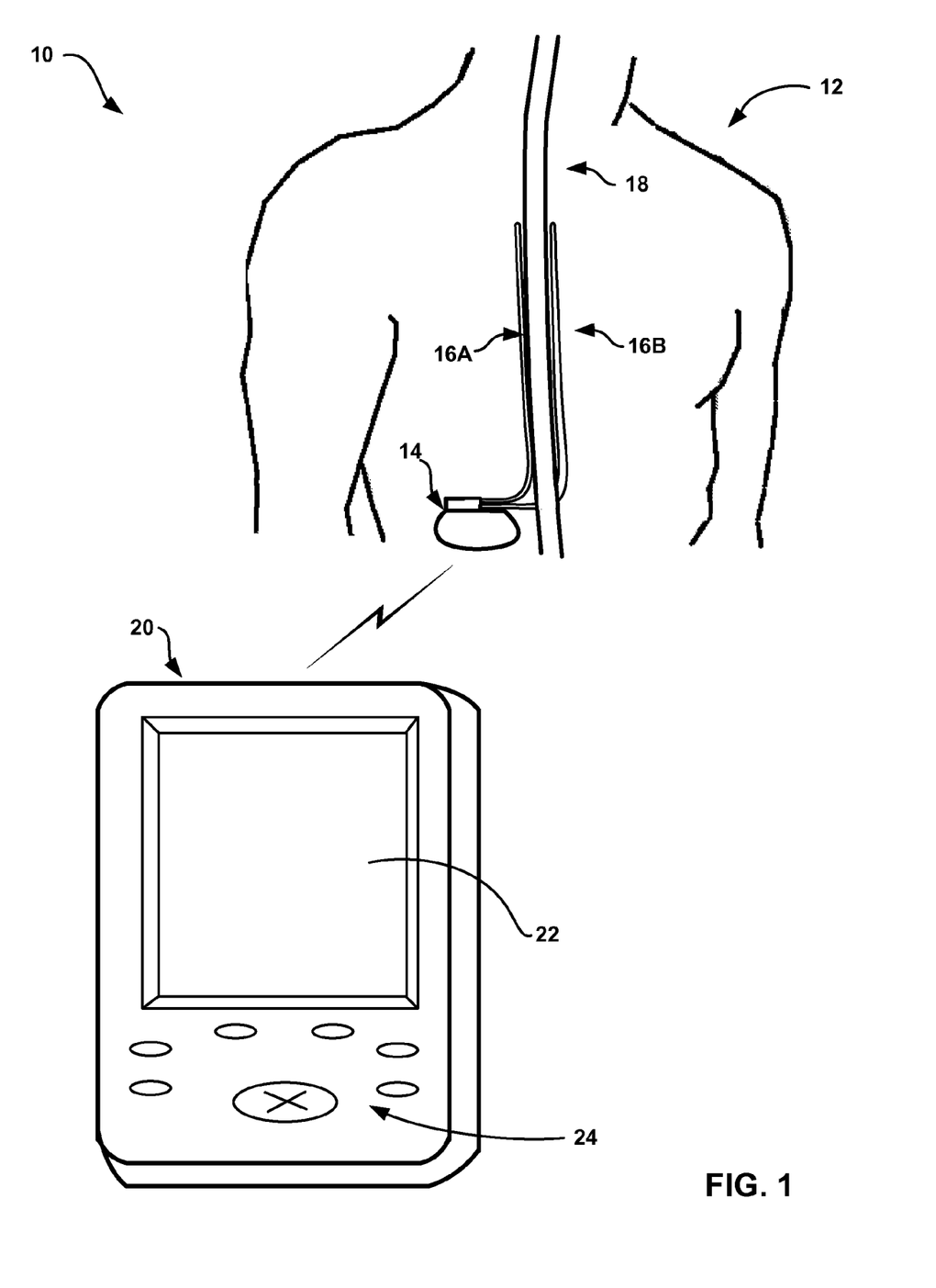
FIG. 1 is a diagram illustrating a system for programming and delivering neurostimulation therapy.

FIG. 1 is a diagram illustrating an example system 10 for programming neurostimulation therapy for and delivering neurostimulation therapy to a patient 12. System 10 includes an implantable medical device (IMD) 14 that delivers neurostimulation therapy to patient 12. IMD 14 may be an implantable pulse generator, and may deliver neurostimulation therapy to patient 12 in the form of electrical pulses. System 10 makes use of decision trees for selection of parameter configurations, such as electrode configurations.

IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown), sacrum (not shown) or stomach (not shown), and IMD 14 may deliver neurostimulation therapy to treat incontinence, sexual dysfunction, or gastroparesis.

IMD 14 delivers neurostimulation therapy to patient 12 according to one or more neurostimulation therapy programs. A neurostimulation therapy program may include values for a number of parameters, and the parameter values define a parameter configuration for delivery of the neurostimulation therapy delivered according to that program. In embodiments where IMD 14 delivers neurostimulation therapy in the form of electrical pulses, the parameters may include pulse voltage or current amplitudes, pulse widths, pulse rates, durations and the like. Further, each of leads 16 includes electrodes (not shown in FIG. 1), and the parameters for a program may include information identifying which electrodes have been selected for delivery of pulses according to the program, and the polarities of the selected electrodes. Hence, a parameter configuration may involve one or more of a variety of parameters including electrode configuration, amplitude, pulse width, pulse rate, and duration. Although the invention may be applicable to neurostimulation parameter configuration in general, including configuration of parameters such as amplitude, pulse width, pulse rate, duration and electrode configuration, the invention generally will be described for purposes of illustration in the context of determining an electrode configuration.

A selected subset of the electrodes located on leads 16 and the polarities of the electrodes of the subset collectively define an "electrode configuration." The electrodes may be arranged in a standard inline lead configuration, or as a surgical paddle lead, grid or other format. The electrodes may be associated with different target regions within a body of a patient. Electrode configurations refer to combinations of single or multiple cathode electrodes and single or multiple anode electrodes. Stimulation current flows between the cathodes and anodes for delivery of neurostimulation therapy. Hence, the polarities of the individual electrodes are another feature of the electrode configuration. Electrodes forming part of an electrode configuration may reside together on a single lead or on different leads.

System 10 also includes a programmer 20. Programmer 20 may, as shown in FIG. 1, be a handheld computing device. Programmer 20 includes a display 22, such as a LCD or LED display, to display information to a user. Programmer 20 may also include a keypad 24, which may be used by a user to interact with programmer 20. In some embodiments, display 22 may be a touch screen display, and a user may interact with programmer 20 via display 22. A user may also interact with programmer 20 using peripheral pointing devices, such as a stylus or mouse. Keypad 24 may take the form of an alphanumeric keypad or a reduced set of keys associated with particular functions.

A clinician (not shown) may use programmer 20 to program neurostimulation therapy for patient 12. In particular, the clinician may use programmer 20 to create neurostimulation therapy programs. As part of the program creation process, programmer 20 allows the clinician to identify parameter configurations that enable IMD 14 to deliver neurostimulation therapy that is desirable in terms of, for example, symptom relief, coverage area relative to symptom area, and side effects. Programmer 20 may also allow the clinician to identify parameter configurations that enable IMD 14 to deliver effective neurostimulation therapy with desirable device performance characteristics, e.g., low battery consumption. In addition, techniques as described herein may used to optimize therapy over the course of use of a chronically implanted IMD, e.g., by interaction between patient 12 and a patient programmer to record efficacy observations over time. In this case, a programmer carried by the patient may incorporate some or all of the functionality attributed to programmer 20 as described herein, including functionality designed to assist in identification of parameter configurations using decision trees.

Programmer 20 controls IMD 14 to test parameter configurations in order to allow a clinician to identify desirable parameter configurations in an efficient manner. As will be described in greater detail below, in some embodiments, programmer 20 selects parameter configurations to test based on an electrode configuration search algorithm, as described herein. In particular, according to such an algorithm, programmer 20 may first control IMD 14 to test one or more electrodes to identify a first electrode configuration, and then test other electrode configurations based on guidance built into the search algorithm.

Other neurostimulation parameters such as amplitude, pulse width, pulse rate, and duration also may be evaluated with the electrode configuration. For example, various parameters may be observed simultaneously with observation of each electrode configuration. Alternatively, once a smaller set of electrode configurations has been identified as providing efficacy for a given baseline set of amplitude, pulse width and pulse rate, then different amplitude, pulse width and pulse rate parameters may be iteratively observed for that smaller set of electrode configurations. By controlling IMD 14 to test electrode configurations in an intelligent manner, programmer 20 allows the clinician to more quickly identify desirable electrode configurations. Duration of the delivery of neurostimulation energy also may be observed. In this manner, amplitude, pulse width, and pulse rate parameters need not be evaluated for every electrode configuration, and especially those electrode configurations that are eliminated from consideration by the decision tree.

By controlling IMD 14 to test parameter configurations in an intelligent manner, programmer 20 allows the clinician to more quickly identify desirable parameter configurations, reducing the overall amount of time the clinician spends programming neurostimulation therapy for patient 12. For example, in contrast to existing neurostimulation programming systems that present electrode configurations in a random order or idiosyncratic search methodologies employed by clinicians, programmer 20 may select electrode configurations to test in a way that is more likely to enable desirable configurations to be selected earlier in the search. Consequently, the clinician may be able to end the search before all potential electrode combinations have been tested if one or more desirable configurations have already been identified, saving the amount clinician and patient time required to achieve an efficacious electrode configuration. In addition, with the invention, it may be possible to identify optimal or near optimal parameter configurations that otherwise might not be identified by the clinician.

Even if the clinician elects to test all potential electrode combinations, e.g., if the electrode set is small enough to make testing all electrode configurations practical, programmer 20 may reduce the time required to identify desirable electrode configurations by automating selection of each new configuration to test. Additionally, programmer 20 may improve the search process by collecting efficacy information for each combination tested. As will be described in greater detail below, programmer 20 may present a list of electrode configurations to the clinician, ordered according to the efficacy information, allowing the clinician to more easily identify and select desirable configurations. This list of electrode configurations may be ordered and updated according to newly observed efficacy information as additional electrode configurations are evaluated. Similar techniques may be applied for other neurostimulation parameters forming part of a parameter configuration, such as amplitude, pulse width, pulse rate, and duration.

In order to control IMD 14 to test electrode combinations, programmer 20 may communicate with IMD 14 via telemetry techniques known in the art. For example, programmer 20 may communicate with IMD 14 via an RF telemetry head (not shown). Information identifying desirable combinations of electrodes identified by the clinician may be stored as part of parameter configurations associated with neurostimulation therapy programs. Neurostimulation therapy programs created by the clinician using programmer 20 may be transmitted to IMD 14 via telemetry, and/or may be transmitted to another programmer (not shown), e.g., a patient programmer, that is used by patient 12 to control the delivery of neurostimulation therapy by IMD 14.

Figure 2:
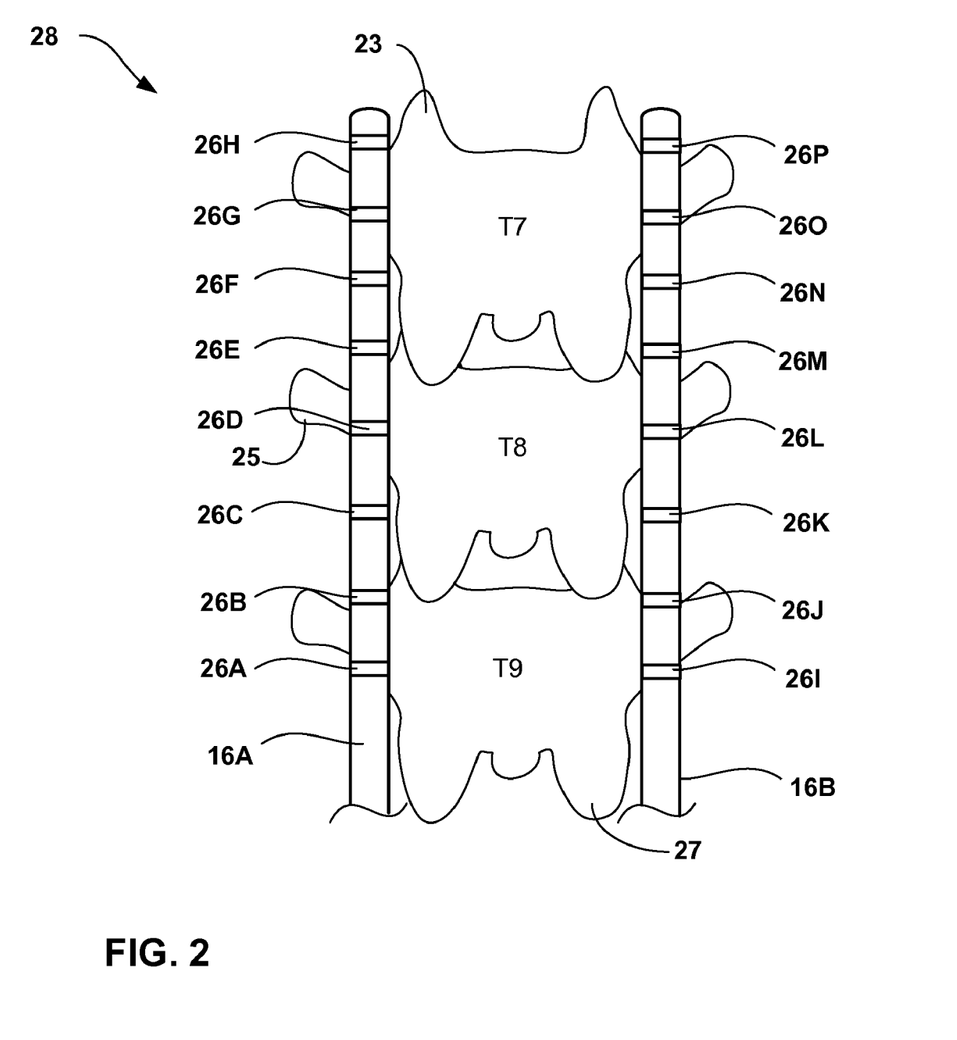
FIG. 2 is a diagram illustrating an example electrode set implanted proximate to the spine of a patient.

FIG. 2 is a block diagram illustrating an example configuration of leads 16. In the example configuration, lead 16A includes electrodes 26A-26H, and lead 16B includes electrodes 26I-26P. Hence, each lead 16 includes eight electrodes, although a lesser or greater number of electrodes are possible. Electrodes 26A-P (collectively "electrodes 26") may be ring electrodes. Electrodes 26 collectively form an electrode set 28 implanted within patient 12. As shown in FIG. 2, electrode set 28 includes eight electrodes on each of the two leads 16, which, as shown in FIG. 1, are implanted such that they are substantially parallel to each other and spinal cord 18 (FIG. 1), on substantially opposite sides of spinal cord 18, at approximately the same height relative to spinal cord 18, and oriented such that the distal ends of leads 16 are higher relative to the spinal cord than the proximal ends of leads 16. Therefore, the illustrated configuration of electrode set 28 may be described as a two-by-eight, side-by-side, upwardly oriented configuration. Of course, electrode set 28 is provided for purposes of example, and the invention may be applicable to other types of leads and electrode sets, including single lead electrode sets, flat paddle leads, grid arrays, and the like.

Such an electrode set is commonly used to provide SCS therapy. However, programmer 20 may be used to identify desirable combinations of electrodes within electrode sets that are configured in any way, and used to provide any type neurostimulation therapy. For example, a single lead including four or eight electrodes, two leads including four electrodes per lead, in-line leads, and offset leads, all of which may be oriented in any manner relative to patient 12, provide electrode set configurations that may be searched by programmer 20. In the example of FIG. 2, electrodes 26 are placed on opposite sides of the T7 vertebra 23, T8 vertebra 25 and T9 vertebra 27 of a human spine.

IMD 14 (FIG. 1) may deliver neurostimulation via any combination of electrodes 26. IMD 14 may independently activate each electrode 26 of set 28 to act as a cathode or anode for a configuration, and each configuration will include at least one cathode and at least one anode. In some embodiments, it is possible that an electrode configuration may include a single electrode 26 acting as the cathode, with a can of IMD 14, i.e., the IMD housing, acting as the anode for the configuration.

In an electrode configuration, electrons flow from one or more electrodes acting as anodes for the configuration to one or more electrodes acting as cathodes for the configuration. The current between anodes and cathodes stimulates neurons between and proximate to the anodes and cathodes. Generally speaking, an electrode configuration enables desirable neurostimulation therapy when current is delivered in a direction and with an intensity sufficient to stimulate specific neurons or a sufficient number of specific neurons to alleviate a symptom without causing unacceptable side effects. Further, an electrode configuration enables desirable neurostimulation therapy when the symptom is alleviated without resorting to undesirably high pulse amplitudes.

As mentioned above, programmer 20 selects individual electrodes 26 or electrode configuration to test to allow a clinician to identify desirable electrode configuration according to an electrode search algorithm. Programmer 20 may select an appropriate search algorithm based on the configuration of electrode set 28, and may select electrodes 26 or electrode configurations based on the selected search algorithm. Programmer 20 controls IMD 14 to test a selected electrode 26 or electrode combination by controlling IMD 14 to deliver neurostimulation via the selected electrode 26 or combination.

In some embodiments, programmer 20 may first control IMD 14 to test one or more of electrodes 26 individually to identify the individual electrode or electrodes 26 which will act as a first cathode. In other embodiments, programmer 20 starts with a combination of selected electrodes 26. Generally, a clinician implants leads 16 in a location such that the center of electrode set 28 is proximate to an area that the clinician believes should be stimulated in order to alleviate symptoms. Therefore, programmer 20 may test electrodes 26 as the first cathode in an order such that electrodes 26 located centrally within electrode set 28, e.g., electrodes 26D-E and 26L-M illustrated in FIG. 2, are tested before peripherally located electrodes. If the clinician's estimation of the target region is inaccurate, programmer 20 will continue to test individual electrodes 26 in such an order until one of the electrodes 26 that enables desirable neurostimulation therapy when activated as the first cathode is identified. Initially locating a first cathode provides a "coarse" optimization of electrode combinations, allowing programmer 20 and the clinician to quickly identify the general area to which neurostimulation therapy should be delivered.

Programmer 20 may then control IMD 14 to test electrode configurations that include the first cathode. The various electrode configurations may be tested with a common set of stimulation parameters, such as a common voltage or current amplitude, frequency, and pulse width. In some embodiments, a series of different stimulation parameters may be applied for each combination of electrodes to test not only the efficacy of electrode combinations, but also electrode combinations with particular stimulation parameters such as amplitude, frequency and pulse width. Hence, an electrode configuration may apply to the combination of electrodes forming part of the neurostimulation parameter configuration, and the parameters associated with delivery of neurostimulation energy via the electrodes, such as amplitude, pulse width and pulse rate, may form another part of the parameter configuration.

Programmer 20 may control IMD 14 to try different ones of electrodes 26 as the first anode in a pair with the first cathode, and may add additional anodes and/or cathodes. In accordance with an embodiment of the invention, programmer 20 controls IMD 14 to test remaining electrodes 26 as first anodes, and additional anodes or cathodes, based on electrode configurations identified by a decision tree. The decision tree may be employed by programmer 20 to allow a clinician to select electrode configurations, and then program IMD 14 to can lead to optimum electrode configurations.

The search algorithm uses the decision tree to select possible electrode configurations based on the efficacies of electrode configurations already observed in the course of evaluation. The previous observations are used to build the structure of the decision tree. The decision tree structure can be obtained from an existing set of data, and can be updated based on efficacy information for newly considered electrode configurations. In particular, the decision tree structure may be updated based on new observations obtained for electrode configurations during the search. The decision tree structure may be updated based on efficacy information for a particular patient or a population or class of patients. With the aid of the decision tree, a programmer 20 provides a clinician with suggestions of electrode configurations that are likely to be efficacious given observations already obtained during the selection process. In response, the clinician may select the suggested electrode configurations next. In some cases, the selection of electrode configurations, or other parameters, may be automated in response to suggestions generated using the decision tree. In other cases, the selection of the parameter configurations may require human intervention from the clinician, but be aided by the suggestions.

Figure 3:
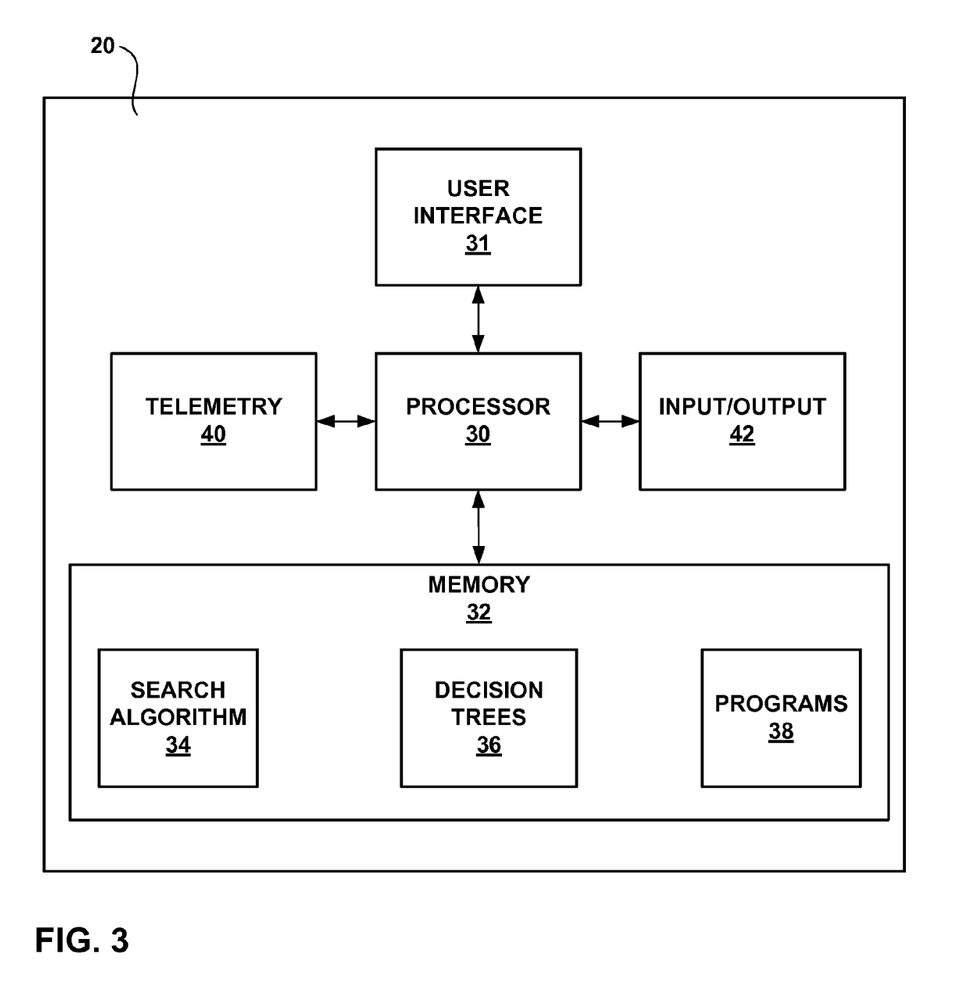
FIG. 3 is a block diagram illustrating a programming device used to identify desirable parameter configurations for neurostimulation therapy programs.

FIG. 3 is a block diagram illustrating an example configuration of programmer 20. A clinician or other user may interact with a processor 30 via a user interface 31 in order to identify and select electrode configurations as described herein. User interface 31 may include display 22 and keypad 24 (FIG. 1), and may also include a touch screen or peripheral pointing devices as described above. Processor 30 may also provide a graphical user interface (GUI) via user interface 31 to facilitate interaction with a clinician, technician, or other medical personnel. Processor 30 may include a microprocessor, a controller, a DSP, an ASIC, an FPGA, discrete logic circuitry, or the like.

Clinician programmer 20 also includes a memory 32. Memory 32 may include program instructions that, when executed by processor 30, cause clinician programmer 20 to perform the functions ascribed to clinician programmer 20 herein. For example, processor may execute one or more parameter configuration search algorithms 34 stored within memory 32. In particular, processor 30 may execute an electrode configuration search algorithm to select individual electrodes 26 or electrode combinations to test to allow the clinician to identify desirable electrode combinations using decision trees. Search algorithm 34 executes based on the content of a decision tree 36, which directs programmer 20 to electrode configurations within electrode set 28 with expected efficacy.

Hence, programmer 20 provides interactive guidance to a clinician during the process of optimizing implantable device parameters. In particular, programmer 20 guides the clinician by suggesting the electrode configurations that are most likely to be efficacious given the results of tests already performed during the source of an evaluation session. This is accomplished by building the decision tree based on the previous results.

Decision trees are useful for classifying observations in a data set based upon one or more attributes or fields within the data. Trees can be built by hand by experts in the field of neurostimulation or can be learned from the data sets themselves using known algorithms for building classification models, such as ID3, C4.5, and the like. In accordance with the invention, programmer 20 uses hierarchical decision trees, either learned or designed, to guide the process of parameter optimization.

The data set used to build the tree includes parameter configurations matched with observed ratings of efficacy on patients of a similar symptomatic indication. The learned attribute, on which classification occurs, will be the optimum parameter configuration for a given set of rated configurations, which are used for classification.

The decision tree search algorithm may be implemented as a feature on programmer 20. In operation, at the beginning of a session, the user (e.g., a clinician) answer a series of questions regarding the device implanted in the patient, the lead configuration in terms of number of leads and electrodes, and the patient symptomatic indication for therapy. Alternately, this information can be stored as part of the patient record. These attributes inform a first decision tree that serves to select the proper decision tree to perform the parameter optimization, e.g., selection of an electrode configuration or other parameters. Thus, a first tree drives selection of a second tree. This decomposition of the problem allows the sub-trees to be much simpler and more computationally feasible.

Upon selection of a sub-tree for parameter optimization, programmer 20 prompts the user with the attribute at the root of the tree, i.e., a first parameter configuration observation for the user to perform. The search algorithm then collects the efficacy rating given to that configuration by the patient, e.g., based on a balance between therapeutic benefit and undesirable side effects. As examples, efficacy can be observed by verbal feedback from the patient concerning therapeutic benefit and side effects, marking of a pain/parasthesia map, objective measurement using pain rating scales, quantification of side effects, a combination of the forgoing, or other observation techniques. Based upon the efficacy rating, the search algorithm consults the tree and prompts for the next parameter configuration. This process continues until a satisfactory result is obtained or the tree determines that no result is possible.

Figure 4:
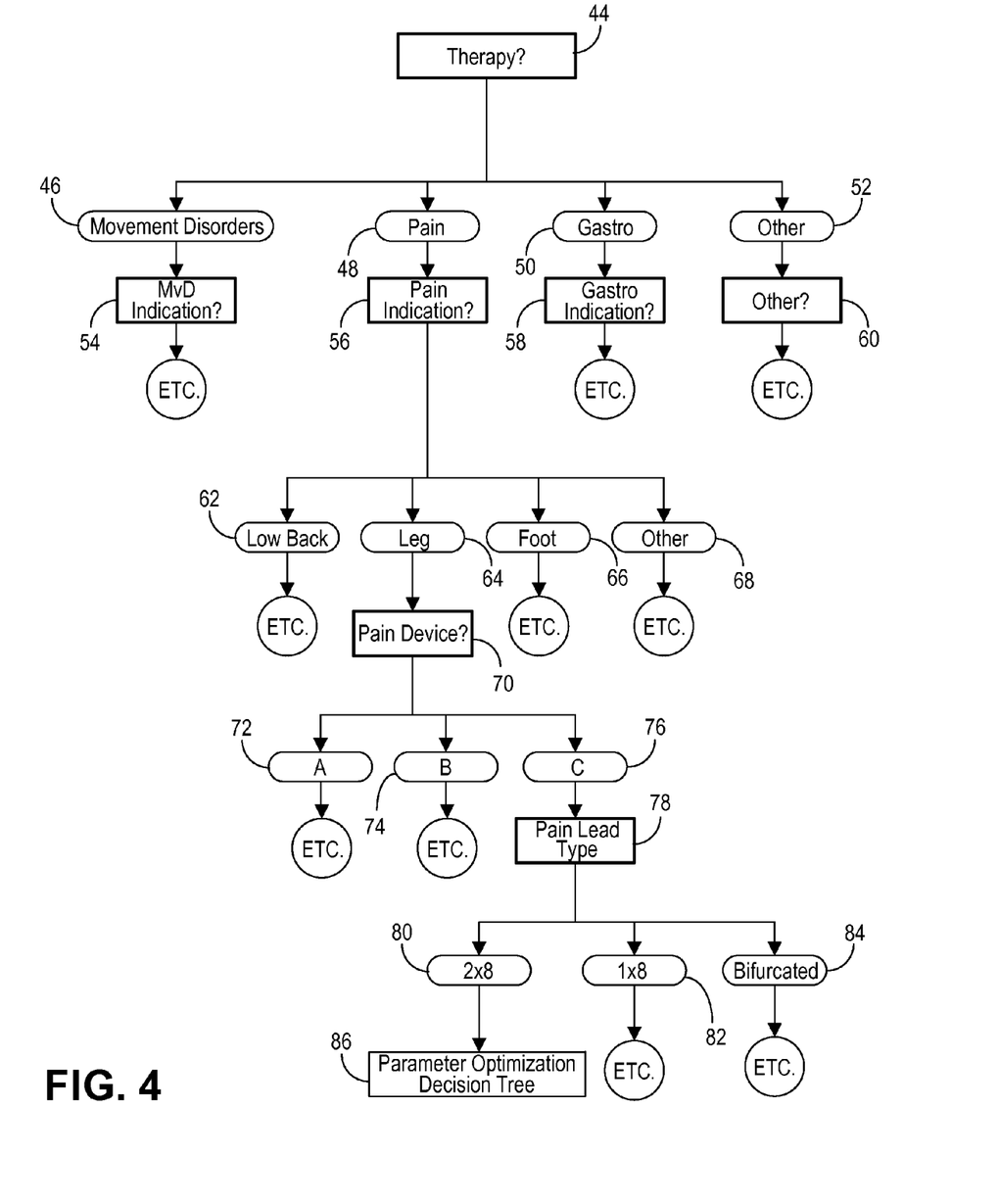
FIG. 4 is a diagram illustrating the structure of a decision tree configured to identify therapy, device and symptomatic indications.
Figure 5:
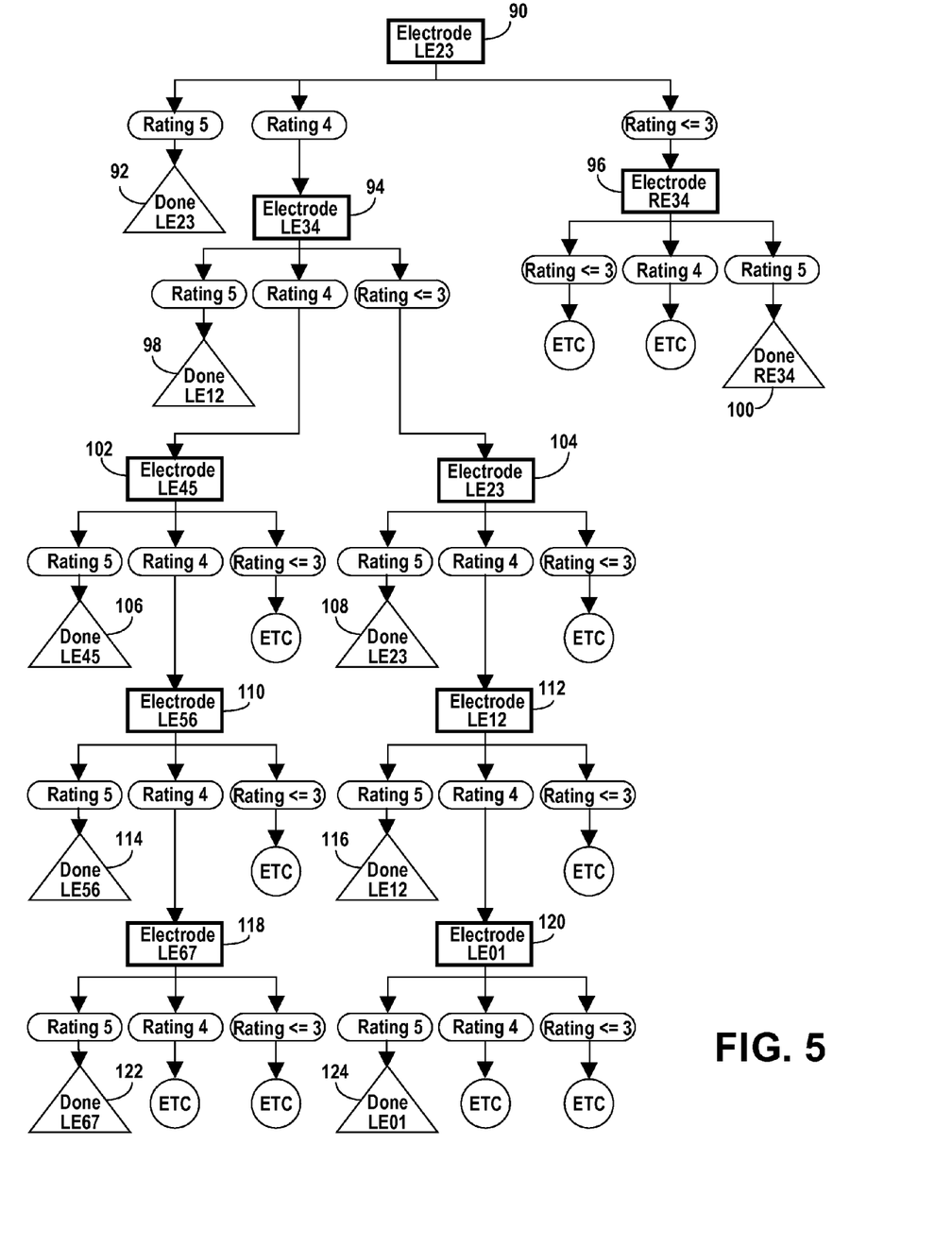
FIG. 5 is a diagram illustrating the structure of a decision tree configured to identify a lead and electrode configuration.

It may be preferable to learn the optimum tree from actual data. For purposes of illustration, however, FIGS. 4 and 5 depict partial decision trees that have been designed by hand. The partial decision trees of FIGS. 4 and 5 address the problem of selecting the optimum electrode configuration. The partial decision tree of FIG. 4 represents a first level of the decision tree hierarchy, and is directed to identification of therapy, device, lead and symptomatic indication. Specifically, the decision tree of FIG. 4 is design to identify the type of neurostimulation therapy (44) to be applied to the patient, e.g., therapy directed to pain relief (46), gastro disorders (48), movement disorders (50), or other disorders (52), such as sexual dysfunction.

Upon identifying the type of therapy, the decision tree of FIG. 4 proceeds to identify the indication presented by the patient, e.g., movement disorder (MvD) indication (54) for movement disorders, pain indication (56) for pain, gastro indication (58) for gastro disorders, or other indications (60). In the case of pain (48, 56), as an example, the decision tree proceeds to identify the particular pain indication, e.g., pain in the lower back (62), leg (64), foot (66), or other area (68).

Next, upon identifying the particular therapy type and indication, the decision tree of FIG. 4 proceeds to identify the type of device implanted in the patient. In the example of FIG. 4, the decision tree determines whether the patient has a device type A (72), B (74), or C (76), which may represent different available neurostimulation devices. The different neurostimulation devices may have different capabilities and target sites, and may be different models within a line of neurostimulation devices.

Upon determination that the patient has an implanted neurostimulation device of type C (76), as an example, the decision tree proceeds to determine the lead configuration for the device, i.e., the pain lead type (78). For example, the decision tree queries whether the patient is implanted with a 2×8 configuration (80) with two leads having eight electrodes each, a 1×8 lead (82), or a bifurcated lead (84). In general, bifurcated lead is split into two identical sets of electrodes. Upon identification of the lead configuration, the search algorithm proceeds to the next "sub" level in the decision tree hierarchy. In particular, the search algorithm proceeds to the parameter optimization decision tree (86) of FIG. 5. Hence, the search algorithm applies a first decision tree to determine a neurostimulation therapy type, neurostimulation device type, lead type and symptomatic indication, and applies a second decision tree based on the determination to select the second parameter configuration. The second decision tree may be one of multiple decision trees directed to different presentations, such as different neurostimulation therapies, neurostimulation device types, lead types and symptomatic indications. The determinations made with a first decision tree as shown in FIG. 4 drive the selection of the appropriate tree for parameter optimization.

As shown in FIG. 5, the parameter optimization tree is generally arranged to identify an optimum electrode configuration in terms of a combination of electrodes that is expected to yield beneficial results for the patient, given the determinations already made by the first decision tree as shown in FIG. 4 with respect to neurostimulation therapy type, neurostimulation device type, lead type and symptomatic indication. The parameter optimization tree also may be configured to evaluate polarities of the electrode combinations forming electrode configurations. In accordance with the invention, a similar parameter optimization tree may be used to identify other parameters within a parameter configuration, which yield satisfactory efficacy. For example, a similar tree may be used for amplitude, pulse width, pulse rate and duration, either independently from the electrode configuration evaluation, or as part of the same process.

The various levels of the parameter optimization tree of FIG. 5 rely on rating information concerning the efficacy of different electrode combinations, e.g., in terms of efficacy and side effects. As examples, efficacy can be observed by verbal feedback from the patient concerning therapeutic benefit and side effects, marking of a pain/parasthesia map, objective measurement using pain rating scales, quantification of side effects, a combination of the forgoing, or other observation techniques.

The decision tree of FIG. 5 is arranged to link upper levels representing given electrode configurations to lower levels that seek to further improve or at test the efficacy of additional electrode configurations in an intelligent manner. Upon traversing the tree structure of FIG. 5, the search algorithm arrives at an electrode configuration or, in some cases, multiple electrode configurations, that offer adequate results, e.g., relative to an efficacy rating threshold.

For example, the decision tree of FIG. 5 may start with a root node such as electrode combination LE23 (90), i.e., a combination of second and third electrodes on a left hand lead. In some embodiments, the combination may also designate a polarity. For example, the electrode combination LE23 may designate the second electrode as the cathode and the third electrode as the anode in the combination. If the combination produces a satisfactory efficacy rating, the process terminates (92). In this case, electrode combination LE23 is selected. The example of FIG. 5 uses a rating scale of 1 to 5, with 5 being best and 1 being worst. In some embodiments, nodes with ratings of less than 3 may be discarded, rather than expanded. If a rating of 5 is not achieved, then the root node 90 may be expanded to explore other combinations. In FIG. 5, ratings of 4 and 3 yield evaluation of additional next-level nodes 94, 96 directed to electrode combinations LE34 and RE34. The next-level nodes may be determined by an expert in the neurostimulation domain in building the tree or learned from data. Also, the tree may be updated over time based on past observations of efficacy for particular parameter configurations, either for a particular patient or a class of patients for which the decision tree is formulated. Classes of patients may be determined based on particular presentations of symptoms, age, health, gender, size, and the like.

Nodes 94 and 96 may be similarly expanded and rated to yield final electrode configurations 98, 100, or additional nodes 102, 104 in the case of node 94. The process may continue, yielding nodes 110 112, final electrode configurations 114, 116, additional nodes 118, 120, final electrode configurations 122, 124, and so forth, depending on which branch of the tree is traversed based on the rating information. In some embodiments, branches with higher ratings may be traversed before branches with lower ratings. For example, a branch with a node rating of 4, such as the branch stemming from node 94 may be evaluated before a branch with a node rating of 3, such as the branch stemming from node 96.

If a particular branch yields an electrode configuration with a satisfactory rating, such as 5, it is not necessary to consider the other branches. In this case, the other branches are considered only if previous branches have not yielded an electrode configuration with satisfactory efficacy results, i.e., efficacy that satisfies an efficacy threshold. Alternatively, a user may desire to evaluate all or some of the additional branches before making a decision. In each case, an iteration limit may be employed to limit the depth of iteration within the tree, including the depth of expansion along a particular branch.

Processor 30 collects information relating to the parameter configurations identified by the decision trees of FIGS. 4 and 5, and stores the information in memory 32 for later retrieval and review by the clinician to facilitate identification of desirable parameter configurations. Neurostimulation therapy programs 38 created by the clinician may be stored in memory 32, and information identifying electrode configurations selected by the clinician to be utilized for one of programs 38 may be stored as part of the programs 38 within memory 32. Memory 32 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like. Again, memory 32 or other computer-readable media may also store instructions to cause processor 30 to perform techniques for selection of parameter configurations for a neurostimulator, as described herein.

Processor 30 controls IMD 14 to test selected individual electrodes 26 or electrode combinations, by controlling IMD 14 according to the decision tree to deliver neurostimulation therapy to patient 12 via the selected individual electrodes 26 or electrode combinations via a telemetry circuit 40. Processor 30 may transmit programs 38 created by the clinician to IMD 14 via telemetry circuit 40, or to another programmer used by the patient to control delivery of neurostimulation therapy via input/output circuitry 42. I/O circuitry 42 may include transceivers for wireless communication, appropriate ports for wired communication or communication via removable electrical media, or appropriate drives for communication via removable magnetic or optical media.

Using the decision tree structure, programmer 20 provides suggestions on which electrode configurations are most likely to be efficacious. In this manner, the decision trees can be used to guide the clinician to a set of optimum parameter configurations, such as electrode configurations, for evaluation, thereby reducing the number of observations that need be made to ensure a good outcome. In other words, the decision trees may permit the clinician to avoid a number of electrode configurations that, based on previous experience, are unlikely to yield efficacious results. Rather, the hierarchical structure of the decision tree leads to particular electrode configurations that have been determined, from past observations, to be more likely to produce optimum efficacy results.

Figure 6:
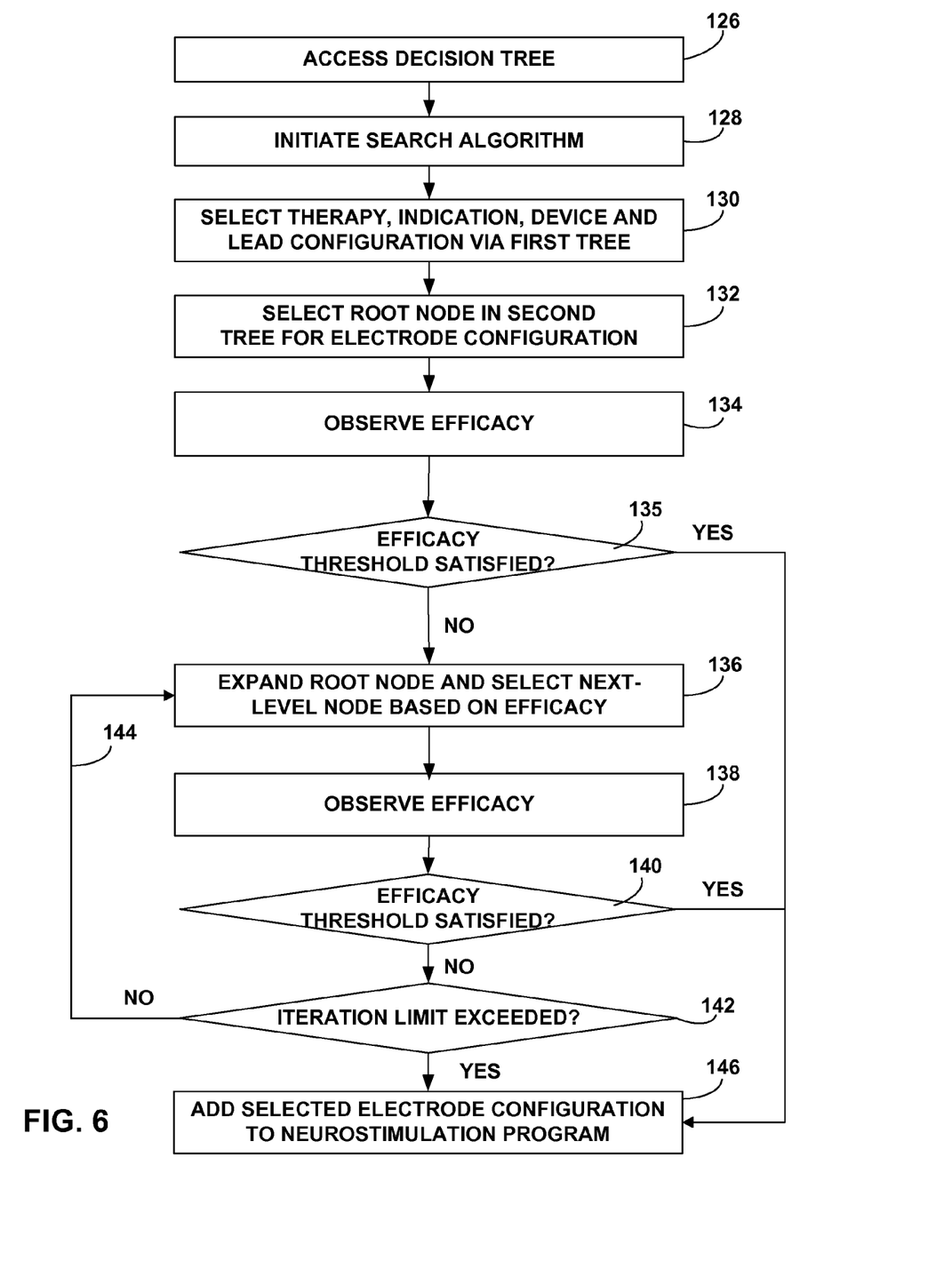
FIG. 6 is a flow diagram illustrating a search algorithm that is executable by a programmer to select electrode configurations using a decision tree.

FIG. 6 is a flow diagram illustrating a search algorithm that is executable by a programmer to select parameter configurations using decision trees as described herein. The example of FIG. 4 is directed to electrode configurations for purposes of illustration. As shown in FIG. 6, the algorithm involves accessing a decision tree (126) that has been built for a parameter optimization problem, such as identification of an electrode configuration. Again, the decision tree may be built manually or through automated techniques. Upon initiating the search algorithm (128), a first tree is used to select therapy, indication, device and lead configuration (130). On this basis, the algorithm selects a second tree and, more particularly, selects a root node in the second tree (132). The root node corresponds to a first electrode configuration, and may be determined based on pain and region indications obtained from the first tree. Alternatively, a user may select the root node.

Upon receiving an indication of observed efficacy of the electrode configuration associated with the current node (134), the algorithm determines whether an efficacy threshold is satisfied (135). If the efficacy threshold is satisfied, the algorithm terminates and proceeds to add the selected electrode configuration associated with the current node in the decision tree to a neurostimulation program stored by programmer 20. Again, the efficacy may be rated positively in terms of pain relief or other therapeutic benefit, and negatively in terms of side effects of the therapy. The search capability can be implemented as a feature in an implantable device programmer 20. If the efficacy threshold is not satisfied (135), the process expands the root node to select a next-level node based on an indication of observed efficacy (136). For example, as indicated in FIG. 5, one of several next-level nodes may be selected based on the efficacy rating of the root node.

The process then observes the efficacy of the next-level node (138). If the efficacy threshold is satisfied (140), the electrode combination associated with the next-level node is selected and added to the neurostimulation program (146). If the efficacy threshold is not satisfied (140), and an iteration limit has been exceeded (142), the algorithm terminates. In this case, the current electrode configuration may be selected and added to a neurostimulation program (146), or the clinician may be prompted to take other action. If the iteration limit is not exceeded (142), the decision tree process continues iteratively (144) until the efficacy threshold is satisfied or the iteration limit is exceeded. The iteration limit may be established by the clinician, or defined by the depth of the applicable decision tree. In some embodiments, the clinician may elect to manually terminate the algorithm.

If the clinician stops the search before all possible combinations of electrodes 26 have been tested, programmer 20 may create a bracket of untested combinations that the clinician may elect to include in neurostimulation therapy programs. The bracket may consist of any number of electrode combinations, and may comprise the next n combinations that would have been tested according to the electrode combination search algorithm. By providing the clinician with a bracket, programmer 20 may allow clinician to spend less time searching for desirable electrode combinations in a subsequent programming session. Specifically, the programs created using the bracket combinations may enable desirable neurostimulation therapy similar to that provided in a program created with the most recently tested combination, and may be provided to patient 12 so that patient 12 can experiment with the bracket programs outside of the clinic.

As described herein, programmer 20 controls IMD 14 to test electrode configurations by controlling IMD 14 to deliver neurostimulation therapy via combinations of electrodes. In addition, programmer 20 may be configured to facilitate a search for other optimum therapy parameters. For example, the clinician or programmer 20 may select desired starting points for pulse amplitude, rate, pulse width, and duration for each electrode configuration, and programmer 20 may ramp the amplitude from the starting point at a first rate of amplitude increase using similar techniques. Programmer 20 may increase the amplitude in, for example, a linear or step-wise fashion. In some embodiments, the clinician or patient 12 may control the rate of amplitude increase. The clinician or patient 12 stops the ramping of the amplitude when the stimulation causes discomfort, or other undesirable side effects.

Programmer 20 may reduce the amplitude at the time the ramp is stopped by some amount, e.g., a percentage, and ramps the amplitude again in order to allow the clinician and/or patient 12 to identify the amplitude that provides the best neurostimulation therapy. This second time, programmer 20 may ramp the amplitude at a slower rate of amplitude increase in order to facilitate identification of the point where best neurostimulation is achieved. Again, in some embodiments, the clinician or patient 12 may control the amplitude.

Programmer 20 stores the amplitude at the time when the best neurostimulation therapy is indicated by the clinician and/or patient 12, and rating information for the electrode combination. The clinician and/or patient 12 may provide efficacy rating information, e.g., a numerical value for one or more metrics for rating the combination, which relates to the efficacy enabled by the combination or the side effects resulting from use of the combination, or both.

The clinician may use rating information and/or the amplitude values stored for each tested combination to identify desirable electrode configurations. The configurations and their associated information and values may be presented in a list that may be ordered according to the information, the values, or a combination of the two. The amplitude value may, for example, be used to distinguish between tested combinations with similar ratings based on the power that must be consumed in order for each combination to enable desirable neurostimulation therapy.

Various embodiments of the invention have been described. However, one skilled in the art will appreciate that various additions and modifications can be made to these embodiments without departing from the scope of the invention. The invention may be generally applicable to any programming optimization problem in which the feedback from a configuration is available relatively quickly and within the context of the clinical programming environment. This includes the stimulation therapies for pain and movement disorders and may include other stimulation-based therapies as well.

For example, although programmer 20 has been described herein as a hand-held computing device, programmer 20 may take the form of any type of computing device, such as a laptop or desktop computer, may access resources, such as memory 54, via a computer network, such as a LAN, WAN, or the World Wide Web. Further, programmer 20 may include a plurality of computing devices, which may communicate to provide the functionality ascribed to programmer 20 herein via a computer network.

Although described herein as associated with and interacting with a clinician, i.e., a clinician programmer, programmer 20 may be associated with patient 12, i.e., a patient programmer. In some embodiments, patient 12 may simply interact with programmer 20 in place of the clinician for some or all of the electrode combination identification process. In other embodiments, patient 12 may perform parts of the configuration identification process without being supervised by the clinician, e.g., away from the clinic, using a patient programmer. These and other embodiments are within the scope of the following claims.

The invention claimed is:

1. A method comprising:
selecting a first parameter configuration for a neurostimulator;
receiving an indication of observed efficacy of the first parameter configuration;
selecting a branch of a decision tree based on the indication of observed efficacy and a position of the first parameter configuration within the decision tree, wherein the decision tree comprises a plurality of nodes and branches and defines a hierarchy of possible parameter configurations for a neurostimulator, wherein each node defines an alternative parameter configuration from each of the other nodes, and each branch links one of the nodes to another of the nodes; and
selecting a second parameter configuration for the neurostimulator based on the selected branch of the decision tree.

2. The method of claim 1, wherein the parameter configurations include electrode configurations, each of the electrode configurations defining a combination of two or more electrodes for delivery of neurostimulation energy.

3. The method of claim 2, wherein each of the electrode configurations defines polarities for electrodes in the combination.

4. The method of claim 2, wherein the electrodes are carried by two or more implanted leads, and the electrodes are associated with different target regions within a body of a patient.

5. The method of claim 4, wherein the leads are implanted proximate a spine of a patient.

6. The method of claim 2, further comprising iteratively selecting additional electrode configurations for the neurostimulator based on the indication of observed efficacy of preceding electrode configurations and positions of the preceding electrode configurations within the decision tree, and terminating the iterative selection of the additional electrode configurations when one or more termination criteria are satisfied.

7. The method of claim 6, wherein the termination criteria include selection of one of the electrode configurations with an observed efficacy that satisfies a threshold efficacy.

8. The method of claim 7, wherein the termination criteria include an iteration limit.

9. The method of claim 2, further comprising:
iteratively selecting additional electrode configurations for the neurostimulator based on observed efficacy of preceding electrode configurations and positions of the preceding electrode configurations within the decision tree;
terminating the iterative selection of the additional electrode configurations at a final electrode configuration when one or more termination criteria are satisfied; and
programming the neurostimulator to employ the final electrode configuration in delivery of neurostimulation therapy.

10. The method of claim 9, wherein the neurostimulator is a spinal cord stimulator, and the final electrode configuration includes electrodes deployed on one more implanted spinal leads.

11. The method of claim 10, wherein the final electrode configuration defines a combination of two electrodes from a set of at least eight electrodes.

12. The method of claim 1, wherein the first parameter configuration includes a first electrode configuration and the second parameter configuration includes a second electrode configuration, wherein the first electrode configuration is defined by a root node in the decision tree, the method further comprising expanding the root node to produce a next-level node defining the second electrode configuration when the observed efficacy for the first electrode configuration does not satisfy a threshold efficacy.

13. The method of claim 12, further comprising receiving an indication of the efficacy of the second electrode configuration defined by the next-level node and further expanding the next-level node to produce one or more additional next-level nodes defining additional electrode configurations until one of the electrode configurations associated with one of the next-level nodes satisfies the threshold efficacy or an iteration limit is reached.

14. The method of claim 1, wherein selecting the first and second parameter configurations includes suggesting the first and second parameter configurations to a user.

15. The method of claim 1, wherein receiving an indication relating to observed efficacy includes receiving user input indicating observed efficacy.

16. The method of claim 1, further comprising updating the decision tree based on the observed efficacy.

17. The method of claim 16, wherein updating the decision tree comprises updating the decision tree based on the observed efficacy for a particular patient.

18. The method of claim 1, further comprising applying a first decision tree to determine a neurostimulation therapy type, neurostimulation device type, lead type and symptomatic indication, and applying a second decision tree based on the determination to select the second parameter configuration.

* * * * *